United States Patent [19]

Kamiya et al.

[11] Patent Number: 5,192,301
[45] Date of Patent: Mar. 9, 1993

[54] CLOSING PLUG OF A DEFECT FOR MEDICAL USE AND A CLOSING PLUG DEVICE UTILIZING IT

[75] Inventors: Tetsuro Kamiya, Suita; Shigeyuki Echigo, Toyonaka; Takehisa Matsuda, Mino; Ryuichiro Yoda, Yokohama; Nobuko Satoh, Kawasaki, all of Japan

[73] Assignee: Nippon Zeon Co., Ltd., Tokyo, Japan

[21] Appl. No.: 754,163

[22] Filed: Sep. 3, 1991

Related U.S. Application Data

[63] Continuation of Ser. No. 460,273, July 2, 1990, ABn.

[30] Foreign Application Priority Data

Jan. 17, 1989 [JP] Japan .................. 1-7916

[51] Int. Cl.$^5$ .............................................. A61B 17/04
[52] U.S. Cl. ................................ 606/213; 606/198
[58] Field of Search .............. 606/198, 213, 215, 191; 128/899, 831, 843; 604/281; 600/32

[56] References Cited

U.S. PATENT DOCUMENTS

| | | |
|---|---|---|
| 4,503,569 | 3/1985 | Dotter .................. 606/191 X |
| 4,512,338 | 4/1985 | Balko et al. ............ 606/191 X |
| 4,728,322 | 3/1988 | Walker et al. .......... 604/164 X |
| 4,744,364 | 5/1988 | Kensey ................. 606/213 |
| 4,840,613 | 6/1989 | Balbierz ............... 604/164 X |
| 4,917,089 | 4/1990 | Sideris ................. 606/215 |
| 4,936,204 | 6/1989 | Landymore et al. ....... 606/215 |
| 4,994,069 | 2/1991 | Ritchart et al. ........ 606/198 X |

FOREIGN PATENT DOCUMENTS

| | | | |
|---|---|---|---|
| 3038928 | 4/1982 | Fed. Rep. of Germany | 128/831 |
| 1417881 | 8/1988 | U.S.S.R. | 604/281 |

*Primary Examiner*—Michael H. Thaler
*Attorney, Agent, or Firm*—Frishauf, Holtz, Goodman & Woodward

[57] ABSTRACT

The closing plug and the closing plug device are used for closing a body defect percutaneously. During the insertion into the defect, the closing plug can be deformed to a smaller size to facilitate the insertion operation and recovered to its original larger shape after it is fitted to the defect, to thereby close the defect. The closing plug device facilitates the insertion of the closing plug into the defect. The closing plug has a flange or an enlarged portion at least at one end thereof and is made of a shape memory polymer having a shape recovery temperature in the range of 20° C. to 70° C. The closing plug device comprises a closing plug, a catheter and a guide wire or a pushing wire to aid in insertion of the closing plug to a defect.

12 Claims, 5 Drawing Sheets

CLOSING PLUG OF A DEFECT FOR MEDICAL USE AND A CLOSING PLUG DEVICE UTILIZING IT

This application is a continuation of application Ser. No. 07/460,273, filed Jan. 2, 1990, now abandoned.

BACKGROUND OF THE INVENTION

1. Field of the Invention

The present invention relates to a closing plug of a defect for medical use which is utilized to close a defect of a somatic wall of a living body, that exists either congenitally or acquiredly.

Cases of defects which require medical treatment are patent ductus arteriosus (PDA), atrial septal defect (ASD), ventricular septal defect (VSD), aneurysm, varix and so on.

In the cases of PDA, ASD and VSD, the defects must be closed by a surgical operation. And in other cases, the pressure of the blood stream must be decreased, because the high pressure of the blood stream which is caused by the existence of an aneurysm or a varix causes bursting of the defective blood vessel.

2. Prior Art

For the treatment of PDA, a thoracotomy is generally performed and the ductus arteriosus is ligated or cut. This operation has many problems. For example, it is dangerous because of the thoracotomy and the scar remains permanently.

For the treatment of an aneurysm or varix, methods of bypassing or utilizing an artificial blood vessel are generally taken. But these methods have a problem, in that the danger is not small.

SUMMARY OF THE INVENTION

Accordingly, it is an object of the present invention to provide a closing plug for therapeutic use within a body duct or defect.

The above described object can be achieved according to the present invention by utilizing:

1. A closing plug which has a flange at least at one end thereof and which is made of a shape memory polymer having a shape recovery temperature in the range from 20° C. to 70° C.;

2. A closing plug which has two flanges, one at each end, and which is made of a shape memory polymer having a shape recovery temperature in the range of 20° C. to 70° C.;

3. A closing plug device which comprises:

(A) a closing plug which is made of a shape memory polymer having a memory recovery temperature in the range from 20° C. to 70° C., and which has a flange at least at one end and a narrow hole through which a guide wire is passed;

(B) a guide wire which passes through the narrow hole of the closing plug so that said plug can slide over the wire; and (C) a pushing catheter which has an inner diameter smaller than that of the closing plug which is shape in a decreased size before the recovery of the original shape; and 4. A closing plug device which comprises:

(A) a closing plug which is made of a shape memory polymer having a memory recovery temperature in the range from 20° C. to 70° C. and which has a flange at least at one end;

(B) a catheter which has an inner diameter larger than the maximum diameter of the closing plug and which is shaped in a decreased size before the recovery of the original shape; and (C) a pushing wire which slides through the inside of the catheter.

BRIEF DESCRIPTION OF THE DRAWINGS

FIG. 10(a) through FIG. 15(b) are views of still other examples of closing plugs of the invention;

DETAILED DESCRIPTION OF THE PREFERRED EMBODIMENTS

Figure 1:
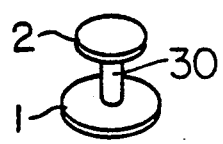
FIG. 1 is a perspective view of a closing plug of the invention.

For the purpose of achieving the above-described object of the invention, the inventors considered that the best method of closing a body defect is to insert a closing plug percutaneously because it does not require surgical operations and intensive investigations were made on the method.

A closing plug is inevitably required to have a structure and a dimension which is suitable for holding and fixing at the body defect but, in general, this kind of structure and dimension makes it difficult to insert the closing plug. Thus, a solution to this contradictory situation was required. To secure the fixing of the closing plug at the defect, a flange or the like must be placed at the end of the closing plug and it must be located on the side of higher fluid pressure. However, in a case like closing a body defect at an aorta and a pulmonary artery, the closing plug is inserted from the side of lower fluid pressure and the insertion of the flange is very difficult to perform percutaneously, because the diameter of the flange is larger than that of the defect.

The inventors came to consider that the only way to solve the above contradictions is to use a plug of small size when it is inserted and which changes to a bigger size when it is fixed in a defect of the body part. For the purpose of achieving this, it was found to be useful that a plug should be made of a shape memory material.

Among various shape memory materials, shape memory polymers are suitable because of their good processability and good adhesion to the somatic wall. Thus, an intensive investigation on the utilization of shape memory polymers led to completion of the present invention.

The kind of shape memory polymer is not particularly limited in the present invention. An example of such polymer is polynorbornene, styrene-butadiene copolymer, polyurethane, transpolyisoprene and the like.

It is essential that the shape recovery temperature of the shape memory polymer utilized in the present invention is in the range from 20° C. to 70° C., preferably in the range from 30° C. to 50° C., because of the relation to the body temperature. When the shape recovery temperature is lower than 20° C., shape recovery is easier to take place during the operation of insertion. And when the shape recovery temperature is higher than 70° C., recovery of the shape at the site of closing a defect is difficult.

In the closing plug, a shape memory polymer is molded to a shape suitable for closing a defect in a body part. The molded closing plug is then deformed to a decreased size suitable to insert easily into the body part above the shape recovery temperature of the polymer and is then cooled to fix the plug to the deformed decreased-size shape. Thus, the deformed closing plug is inserted to the desired location in the body and is then warmed to above the shape recovery temperature to recover the original shape suitable for closing the body defect.

In the closing plug, the operation of the insertion plug and its physical properties are greatly dependent on whether the shape recovery temperature is higher or lower than the body temperature. So, a wide range of requirements which vary by the condition of the defect can be satisfied by choosing a suitable shape recovery temperature of the polymer.

When the shape recovery temperature is lower than the body temperature, it is necessary to cool the closing plug during the insertion in the defective body part and, after fixing the closing plug at the desired location, the original shape of the closing plug is recovered by warming or by the body temperature per se. The closing plug stays in the body as a rubbery and flexible member.

When the shape recovery temperature is higher than the body temperature, cooling during insertion is not required, but is necessary to warm it after the insertion at the desired location to cause it to recover the original shape. After the closing plug is fixed, it is cooled by the body temperature, loses its rubbery flexibility and is fixed to the body as a hard member having a high strength.

If desired, the closing plug can contain a radiopaque material to make it visible to a fluoroscope or other conventional radiographic instrument.

Any kind of a radiopaque material can be utilized so long as it is harmless and has an effect of shielding X-rays. Suitable materials are barius sulfate, tungsten, bismus subcarbonate and the like.

The closing plug comprises a flange at least at one end. The flange prevents the closing plug from slipping through the body defect into the other side of the defect and prevents fluid from flowing through the defect again. For this reason, it is necessary that the size of the flange is larger than that of the body defect.

When the closing plug has a flange only at one end, it is desirable that the flange is fixed at the side of the defect having higher fluid pressure, so that the closing plug does not fall off from the defect.

If desired, the closing plug has two flanges having a diameter larger than that of the defect and holding the defect between the two flanges. In this case, the closing plug does not fall off from the defect even if the fluid pressure in the body changes.

The flange can have any kind of shape so long as the size is larger than that of the body defect to be closed and the flange fits well to the defect. Examples of the shape of the flange are shown in FIG. 1 through FIG. 25.

Figure 2:
FIG. 2, FIG. 6, FIG. 8, FIG. 20 and FIG. 21 are respective side views of other examples of closing plugs of the invention.

A closing plug having a cone shape as shown in FIG. 2 does not have clearly defined Separate flanges. However, the maximum diameter of the cone is larger and the minimum diameter of the cone is smaller than that of the defect to be closed. This closing plug can fit into the defect, and the portion of the maximum diameter acts just in the same way as a flange part and the closing plug can effectively close the defect. Thus, a cone shape is effectively utilized as the closing plug.

If desired, the closing plug has a narrow hole through which a guide wire is passed. When the closing plug has a narrow through-hole, at first, the guide wire is inserted to the location of the defect, the proximal portion of the guide wire is passed through the narrow hole of the closing plug, then a catheter is inserted over the guide wire and the closing plug is pushed into the body by the tip of the catheter along the guide wire. Thus, the closing plug is easily carried to the location of the defect by utilizing the guide wire.

In this application, the shape of the closing plug can be either maintained in the deformed shape or it can be recovered to the original shape by passing a liquid (for example, a physiological saline) at a controlled temperature through the catheter.

The inner diameter of the catheter is naturally larger than the diameter of the guide wire and smaller than the size of the deformed closing plug so that the tip of the catheter can push the closing plug to the location of the defect.

The closing plug having a narrow through-hole cannot close the defect completely because the through-hole remains open. However, the through-hole is so narrow that the closing plug is actually as effective as that without a hole.

The closing plug device comprising the closing plug, the guide wire and the catheter is favorably utilized to achieve the object of the invention.

In another example of the insertion of the closing plug, at first, a guide wire is inserted to the location of the defect, than a catheter is inserted to the location of the defect by utilizing the guide wire, the guide wire is then pulled out and the catheter is left in the body.

The closing plug is shaped to a decreased size to pass through the inside of the catheter, placed into the catheter and transferred to the location of the defect by a pushing wire through the inside of the catheter.

This method has an advantage of controlling the temperature of the closing plug until it reaches the defect by passing a physiological saline through the inside of the catheter and is especially effective when the shape recovery temperature is lower than the body temperature. The inner diameter of the catheter must be larger than the size of the closing plug.

The closing plug device comprising the closing plug, the guide wire and the catheter is favorably utilized to achieve the object of the invention.

The smaller size of the closing plug is more desirable during the insertion. A hollow structure is effectively utilized.

Figure 20:
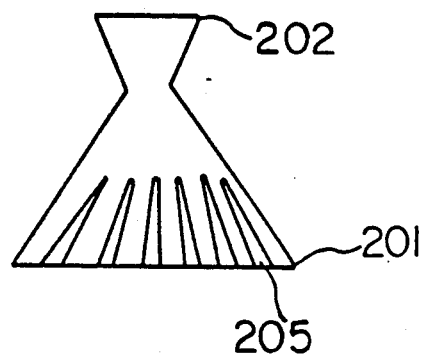
Figure 21:
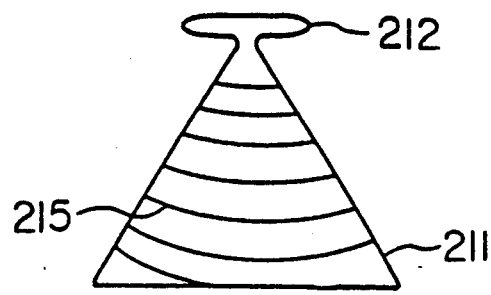
Figure 22:
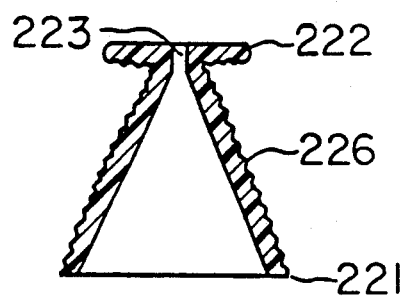

It is desired that the closing plug can have a cut, so that the size of the closing plug can be further decreased. Various kinds of cuts can be utilized. Examples of slits are shown in FIG. 20 and FIG. 21. Smaller dimensions or smaller diameters can be achieved by such cuts.

FIG. 1 shown the basic shape of the closing plug, which as two flanges, 1, 2 of different size, being fixed at both ends of a cylindrical member 30.

The flanges 1, 2 of FIG. 1 are folded inward or outward so that they have a decreased size. After the closing plug is inserted into the defect (i.e., an opening in a body part, the opening having a rim or peripheral edge defining a boundary of the opening), the flanges restore to their original shape as shown in FIG. 1, fix the closing plug to the defect and hold it from both sides of the wall of the body part and, at the same time, the passage of the fluid through the defect stops.

Another shape of the closing plug has a narrow hole along the axis of the cylinder 30, and the size of the hole is wide enough to have a guide wire passed through and slided smoothly. A guide wire can be passed through the hole and the insertion can be facilitated.

FIG. 2 shows a closing plug 40 having a cone shape. The size of the cone is designed so that the size of the defect is smaller than the maximum diameter portion of the cone and larger than the minimum diameter portion of the cone. The larger side of the cone is placed on the side of the defect having a higher fluid pressure, because it works just like a flange, closes the defect and prevents the closing plug from falling off from the defect. The angle at the apex of the cone can be suitably selected depending on the shape of the defect. In general, a sharper angle makes fixing to the defect easier.

Figure 3:
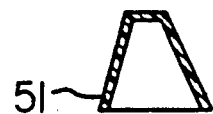
FIG. 3, FIG. 4, FIG. 5, FIG. 7, FIG. 9, FIG. 22 and FIG. 25 are vertical sectional views of still other examples of closing plugs of the invention.

When the cone of FIG. 2 is modified to have a hollow structure 5; as shown in FIG. 3, the size of the closing plug 51 during the insertion can easily be decreased to a greater extent and the closing plug is used more advantageously.

Figure 4:
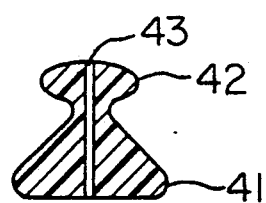

FIG. 4 shows a closing plug having a flange part 41 and an additional flange part 42 at the apex of the cone. The second flange part 42 at the apex of the cone prevents the closing plug from falling off from the defect during pulse variation. The closing plug of FIG. 4 also has an elongated hole 43 therethrough which may be passed over a guide wire as explained above.

Figure 5:
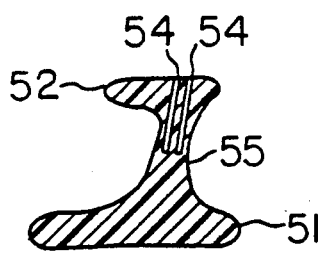

FIG. 5 shows a closing plug having a constriction 55 in the middle portion thereof, an asymmetrical shape to fit well to the shape of the defect and two holes 54 for wires along the axis so that the closing plug can be rotated in the defect before the recovery of the original shape. When a wire has two branches at the front and the branches are inserted into the two holes 54 of the closing plug, the closing plug can be rotated to a desired angle by rotating the wire.

Additionally, the holes 54 are not perforated through the closing plug, so the closing plug closes the defect completely. A closing plug of this shape can be inserted by transferring same through the inside of the catheter. This method will be shown in a later-described example in more detail.

Figure 6:
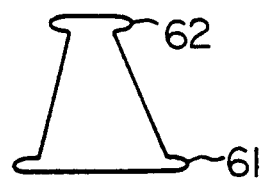
Figure 7:
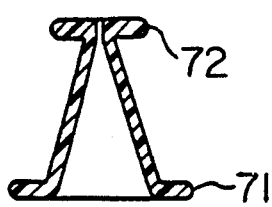

FIG. 6 shows a closing plug having two flanges 61, 62 at the two ends of a cone 63.

Figure 8:
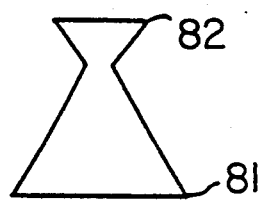
Figure 9:
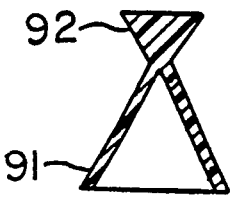
Figure 10:
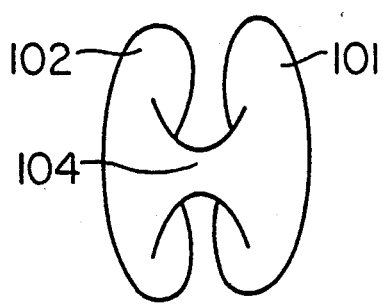
Figure 10:
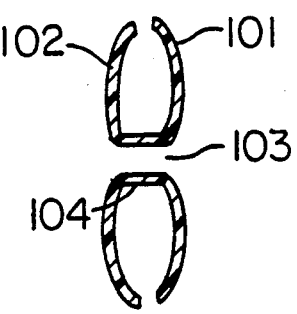

FIG. 8 shows a closing plug having two cones at the two ends 81, 82. This type of the closing plug can be modified to have a hollow structure inside of the larger cone 91, and a smaller solid cone 92, as shown in FIG. 9 so that the size can be decreased more easily.

FIGS. 10(a) and 10(b) show another basic shape of the closing plug. The closing plug comprises two flanges 101, 102 of the same size, connected at two ends of a cylinder portion 104. The two flanges are arranged symmetrically with respect to the middle point of the cylinder 104 and each flange has a shape of a cup which is turned inside out.

Figure 16:
FIG. 16 is an elevational view showing the decreased size of the closing plugs of FIG. 10(a) and FIG. 11(a)

A closing plug having this structure can be inserted while the flanges are folded as shown in FIG. 16. The flanges are recovered to the original shape of FIG. 10(a) when the closing plug is properly fixed to the defect. The flanges 101, 102 hold the defect from both sides and the passage of the body fluid is securely prevented.

If desired, a closing plug of FIGS. 10(a) and 10(b) is modified to have a narrow hole 103 along the axis of the cylinder 104 which is wide enough to have a guide wire passed through smoothly. A guide wire can be passed through the narrow hole to facilitate the operation of the insertion.

Figure 11A:
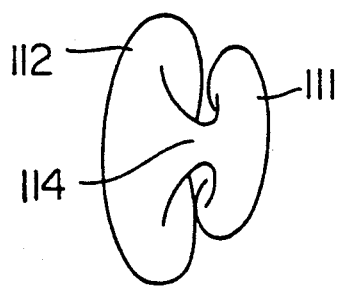
Figure 11:
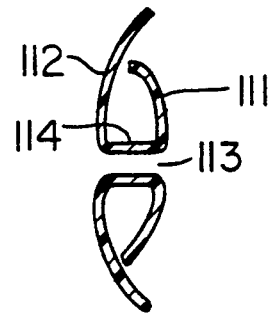
Figure 12:
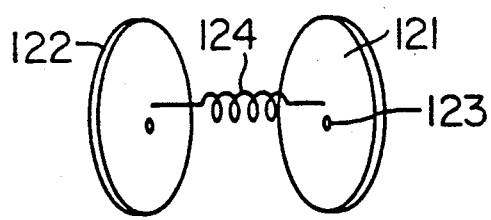
Figure 12:
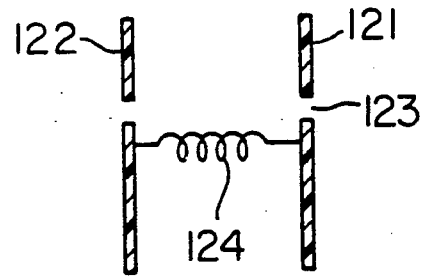
Figure 13:
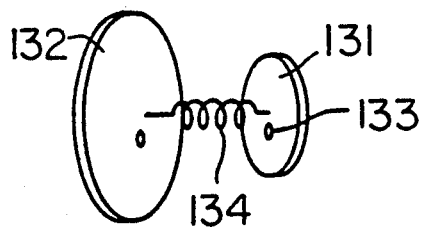
Figure 13:
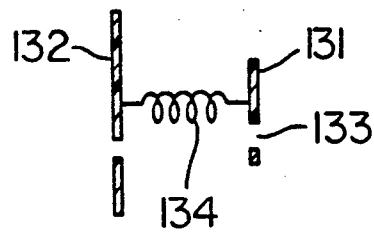

FIGS. 11(a) and 11(b) show a closing plug similar to the structure shown in FIGS. 10(a) and 10(b) except that the structure is not symmetrical and the two flanges 111, 112 on opposite sides of cylinder portion 114 have different sizes. This type of closing plug can be effectively utilized to prevent the closing plug from falling off from the defect by a different pressure between two sides of the wall. A narrow hole 113 can be provided to receive a guide wire.

FIGS. 12(a) and 12(b) show a closing plug comprising two flanges 121, 122 connected to opposite ends of a coil 124 made of a shape memory polymer or a shape memory alloy. Guide wire holes 123 may be provided in flanges 121, 122. The coil is shaped into an elongated form to suit the insertion to the location of the defect. When it is placed into the defect, the coil 124 is warmed to recover to its original shorter length and hold the closing plug tightly from both sides of the wall of the body part. A shape memory alloy is preferable because of the stronger recovery force. The flanges 121, 122 have a disk shape.

FIGS. 13(a) and 13(b) show a closing plug similar to the closing plug of FIG. 12(a) except that the flanges 131, 132, connected between coil 134, are of different sizes so that falling off of the closing plug caused by different fluid pressure between two sides of the wall can be prevented. A guide wire hole 133 may be provided.

Figure 14A:
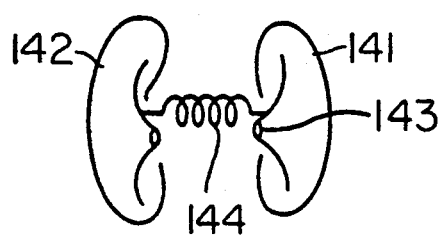
Figure 14B:
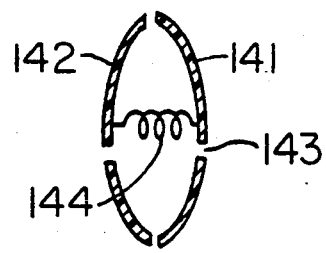

FIGS. 14(a) and 14(b) show a closing plug similar to the closing plug of FIG. 12(a) except that the flanges 141, 142, connected between shape memory coil 144 have a shape similar to those shown in FIG. 10(a). A guide wire hole 143 may be provided.

Figure 15A:
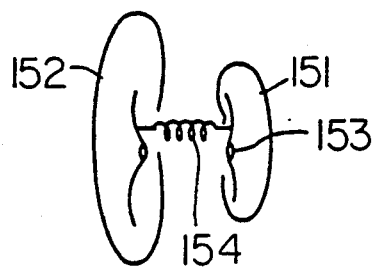
Figure 15B:
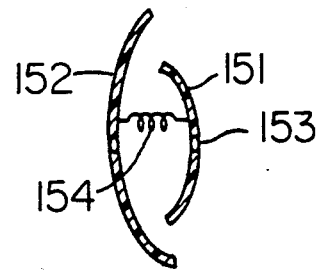

FIGS. 15(a) and 15(b) show a closing plug similar to the closing plug of FIG. 14 except that the flanges 151, 152, connected between shape memory coil 154 are of different sizes. A guide wire hole 153 may be provided.

Figure 17:
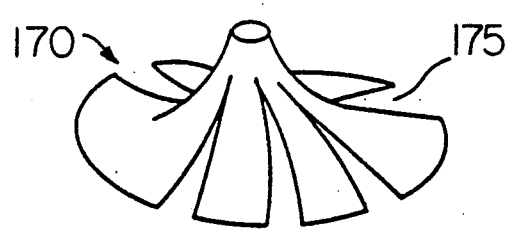
FIGS. 17-19 are perspective views of other examples of closing plugs of the invention.
Figure 18:
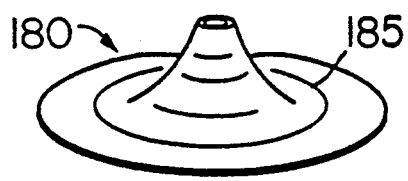

If desired, a closing plug member has cuts on its surface as shown in FIG. 17 and 18 (cuts 175 on member 170 in FIG. 17; cuts 185 on member 180 in FIG. 18), in order to facilitate the insertion. A flange 180 of FIG. 18 can be deformed to a long tape-like shape by the effect of cuts 185.

Figure 19:
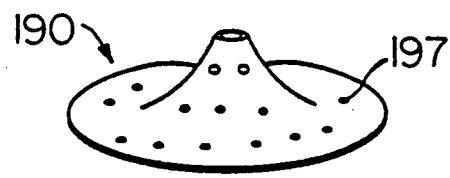

If desired, a closing plug 190 has many through-holes 197 opened on its surface as shown in FIG. 19. As a result, the closing plug 190 can be deformed more easily. In addition, many through-holes 197 allow formation of tissue around the defect after the closing plug is fixed.

FIG. 20 and FIG. 21 show other examples of closing plugs having cuts (205—FIG. 20; 215—FIG. 21) on its surface to make a decreased size or diameter more easily. In the closing plug of FIG. 21, the flange 201 can be deformed tape-like by the effect of the cuts.

The cuts are not limited to those shown in the examples but any kind of cut can be utilized so as to be effective for decreasing the size or diameter of the closing plug.

Figure 23:
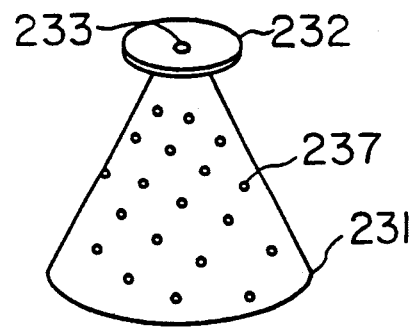
FIG. 23 is an elevational view of still another example of a closing plug, having many holes on its surface.
Figure 24:
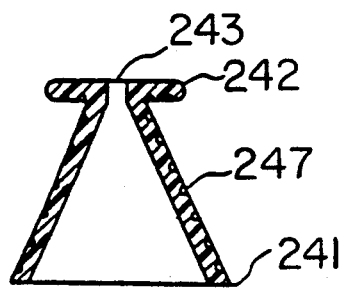
FIG. 24 is a cross-sectional view of the closing plug of FIG. 23.
Figure 25:
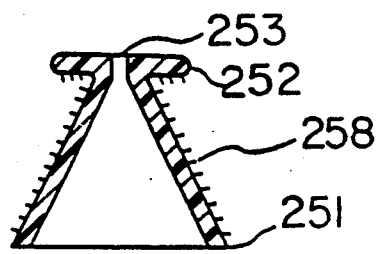

As shown in FIGS. 22 to 25, a closing plug having a rough surface can be favorably utilized for the object of the invention. Any kind of rough surface can be utilized so long as the roughness is effective in fixation. Examples of rough surface structures are a surface having numbers of grooves or continuous protrusions 226 perpendicular to the direction of the axis shown in FIG. 22, a surface having numbers of indentations or isolated protrusions 237 as shown in FIG. 23, a surface having a porous structure like a sponge 247 shown in FIG. 24, a surface having numbers of hairs 258 implanted on the surface thereof as shown in FIG. 25 and the like. Guide wire holes 223, 233, 243, 253 can be provided in the embodiments of FIGS. 22-25, respectively.

If desired, the closing plug can be coated with a biocompatible material, particularly an antithrombogenic material. Such a closing plug may be coated with TEFLON, silicone, polyurethane, or an antithrombogenic polymer such as "cardiothane". Otherwise, antithrombogenic materials such as heparin or urokinase may be combined on the surface of the closing plug.

Figure 26:
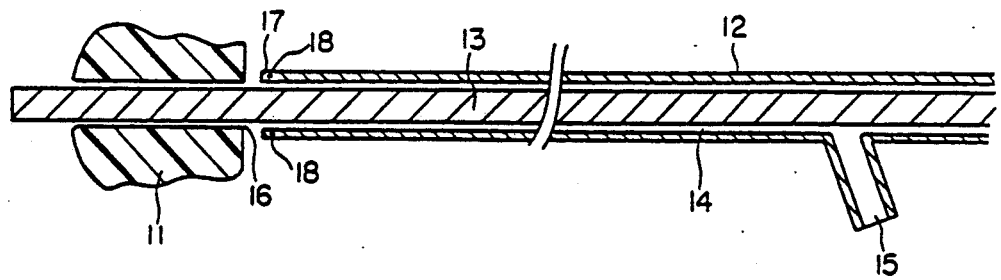
FIG. 26, FIG. 27 and FIG. 28 are cross-sectional views of examples of the closing plug device of the invention, including wires and catheters.

FIG. 26 shows an example of the closing plug device which comprises a closing plug, a pushing catheter and a guide wire for the insertion of the closing plug. The method utilizing the closing plug device is explained in detail in the following.

In the case of the treatment of patent ductus arteriosus, at first, a guide wire is inserted from a femoral vein to the defect between the aorta and pulmonary artery. The guide wire 13 is left at the place. A closing plug prepared from a shape memory polymer having, for example, a shape recovery temperature of 40° C. is deformed to the smaller size 11, the guide wire 13 is pierced through a narrow hole 16 of the closing plug, a catheter 12 is inserted over the guide wire 13 and then, the closing plug 11 is inserted by being pushed by the tip 17 of the catheter 12 until the closing plug reaches the area of the defect.

While the operation can be observed with a fluoroscope, the closing plug is inserted to the defect. Then, fitted to the defect to be closed, physiological saline at a temperature of 45° C. is injected to the catheter 12 through the inlet 15, and the flange is recovered to the original shape and thus the closing plug is tightly fixed to the defect to close it.

The guide wire 13 is removed from the narrow hole by using the catheter 12 the catheter 12 and the guide wire 13 are removed from the body, and the closing plug which has the recovered original shape is left at the defect in the body and thus the treatment is completed.

The closing plug is cooled by the body temperature and becomes gradually a hard material which fits well to the defect.

In the example explained here, a radiopaque material is blended with the shape memory polymer and a thin metallic ring 18 is positioned within the tip of the catheter for the purpose of observing clearly with a fluoroscope. The ring 18 is also useful for the purpose of reinforcement of the tip.

Figure 27:
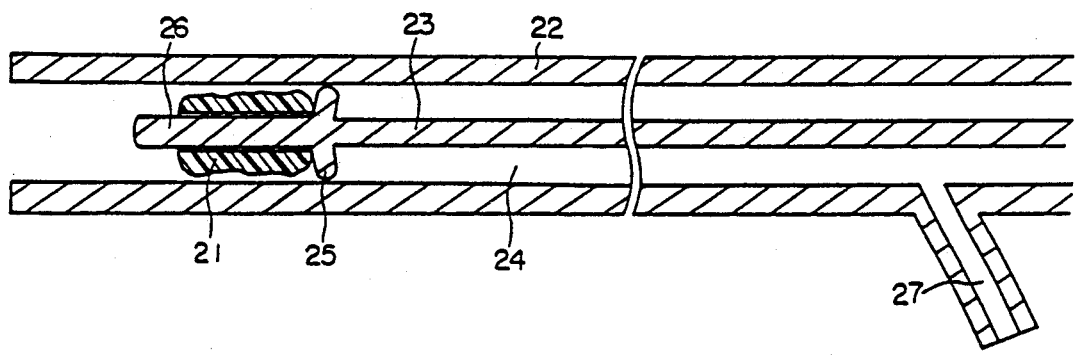

Another example of the closing plug device as shown in FIG. 27 is explained in the following. In this example, at first, a guide wire which is not show in the figure, if necessary is inserted to the defect and a catheter 22 is inserted to the defect along the guide wire in the same way as the previous example shown in FIG. 26. The guide wire is then removed from the body, leaving the catheter in the blood vessel.

Next, the tip of a pushing wire 23 is pierced through a narrow hole of the closing plug and the pushing wire 23 is inserted in the catheter.

In the case of this example, the narrow hole is not required because the closing plug does not slide over the wire as in the case of FIG. 26. It is also convenient when the closing plug has two half-way holes and the pushing wire has two branches at the tip fitted into these two holes. This is because the closing plug can be rotated by rotating the guide wire and the closing plug can be fitted well to the defect.

A shape memory polymer having a shape recovery temperature lower than the body temperature, for example 30° C., can be utilized in this example. The temperature of the closing plug can be accurately controlled by passing physiological saline at a temperature of, for example, 25° C. through the catheter 22 and thus the unfavorable recovery of the original shape during the insertion is securely prevented.

Even when the temperature of the closing plug is increased before the closing plug reaches the defect and the shape of the closing plug begins to expand, the catheter can prevent the closing plug from expanding and the removal of the closing plug is not so difficult.

After the closing plug is fitted to the defect, the shape of the closing plug can be recovered to the original shape by stopping the injection of cold water through the catheter and the hole is closed.

Figure 28:
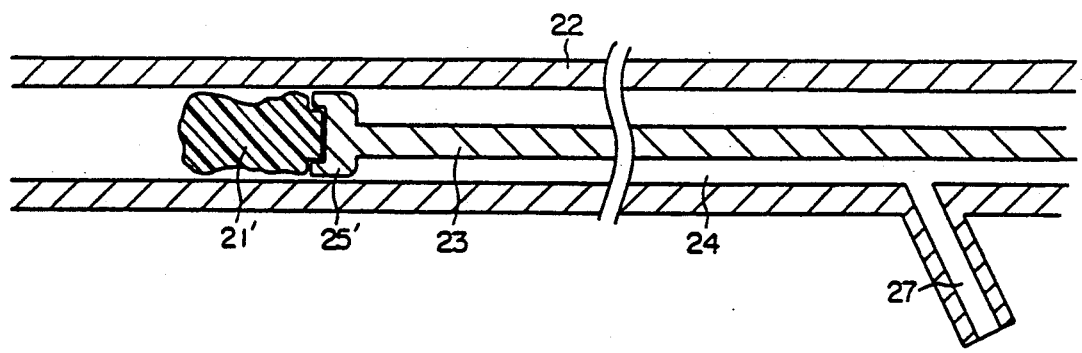

FIG. 28 shows an example of a closing plug device 21' which has no hole. In this example, the tip 25' of the pushing wire 23 comprises a cavity and the closing plug of the invention is deformed to fit in the cavity and be fixed to the cavity by being pushed into it. The closing plug can be rotated to a desired angle by this method.

When the temperature of the closing plug is increased, the closing plug becomes softer and can be removed from the tip of the pushing wire while the closing plug recovers the original shape thereof.

Figure 29:
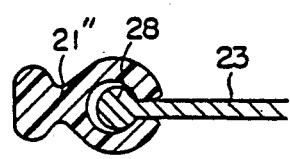
FIG. 29 is a cross-sectional view of a part of the closing plug device of the invention showing the connection of a pushing wire with the closing plug when the closing plug is inserted.

Another example of the connection between the closing plug and the tip of the pushing wire is shown in FIG. 29. A flange having a hollow structure as shown in FIG. 3 or FIG. 9 is deformed so that the flange can wrap around a ball shaped member 28 at the tip of the pushing wire 23. The ball member 28 and the deformed closing plug 21'' are connected as shown in FIG. 29. When the closing plug is allowed to recover the original shape of FIG. 3 or FIG. 9, the closing plug 21'' is disconnected from the ball member 28 at the tip of the pushing wire 23.

When the location of the defect is not far from the inserted position, the closing plug can be inserted and fixed by the tip of the guide wire as described in FIG. 28 and FIG. 29 without using a catheter.

Other structures shown in FIG. 28 are similar to those shown in FIG. 27.

The closing plugs utilized in FIG. 28 or FIG. 27 do not need any passing through-hole, so they can completely close the defect.

In summary, the closing plug of the present invention is made of a shape memory polymer. As a result, the closing plug can be deformed during the insertion and can recover to its original shape when fixed in place.

Also, the closing plug device allows the operation to be carried out percutaneously. Thus, it is useful in medical applications.

We claim:

1. A closing plug for closing an opening in a body part of a living body, said opening in said body part including one of a patent ductus arteriosus (PDA), atrial septal defect (ASD), ventricular septal defect (VSD), aneurysm and varix, said opening having a rim defining a boundary of said opening, and said body part having an interior surface and an exterior surface adjacent said rim of said opening, the closing plug comprising:

a body portion having opposite end portions; and an enlarged portion at each opposite end portion of said body portion, said enlarged portions each having a predefined size and shape which is larger than said opening to be closed and larger than a cross sectional size of said opening to be closed; and wherein at least said enlarged portions are made of a shape memory polymer having a shape recovery temperature in the range of from 20° C. to 70° C., such that at least said enlarged portions are physically able to be reduced in size to a size to freely pass through said opening without further enlarging said opening, prior to introduction into said opening in the body part, and are able to be enlarged to their respective original predefined larger size and shape after insertion through said opening in said body part and after exposure to a temperature within said shape recovery temperature range so that said enlarged portions contact said interior surface and exterior surface, respectively, of said body part adjacent said rim of said opening to close said opening and to prevent said closing plug from coming out of said closed opening;

said closing plug having a narrow through-hole therein, which extends between each of said enlarged portions and which provides effective closure of said opening of said body part, and through which a guide wire is passable between each of said enlarged portions.

2. A closing plug as claimed in claim 1, wherein:
said enlarged portions comprise respective flanges;
said body portion comprises a narrower portion between said flanges;
said narrower portion of the closing plug between said flanges is made of one of a shape memory alloy and a shape memory polymer, such that the length of said narrower portion is able to become shorter when the shape of said narrower portion is recovered after being subjected to the shape recovery temperature.

3. A closing plug as claimed in claim 1, wherein the shape memory polymer contains a radiopaque material.

4. A closing plug as claimed in claim 1, wherein said closing plug has a rough outer surface.

5. A closing plug for closing an opening in a body part of a living body as claimed in claim 4, wherein the enlarged portions have a number of cuts therein.

6. A closing plug as claimed in claim 1, wherein the outer surface of said closing plug is coated with an antithrombogenic material.

7. A closing plug for closing an opening in a body part of a living body as claimed in claim 1, wherein the enlarged portions have a number of cuts therein.

8. A closing plug device which comprises:
(A) a closing plug for closing an opening in a body part of a living body, said opening in said body part including one of a patent ductus arteriosus (PDA), atrial septal defect (ASD), ventricular septal defect (VSD), aneurysm and varix, said opening having a rim defining a boundary of said opening, and said body part having an interior surface and an exterior surface adjacent said rim of said opening, the closing plug comprising:

a body portion having opposite end portions; and an enlarged portion at each opposite end portion of said body portion, said enlarged portions each having a predefined size and shape which is larger than said opening to be closed and larger than a cross sectional size of said opening to be closed; and wherein at least said enlarged portions are made of a shape memory polymer having a shape recovery temperature in the range of from 20° C. to 70° C., such that at least said enlarged portions are physically able to be reduced in size to a size to freely pass through said opening without further enlarging said opening, prior to introduction into said opening in the body part, and are able to be enlarged to their respective original predefined larger size and shape after insertion through said opening in said body part and after exposure to a temperature within said shape recovery temperature range so as to contact said interior surface and said exterior surface, respectively, of said body part adjacent said rim of said opening to close said opening and to prevent said closing plug from coming out of said closed opening;

said closing plug having a narrow through-hole therein, which extends between each of said enlarged portions and which provides effective closure of said opening of said body part, and through which a guide wire is passable between each of said enlarged portions;

(B) a guide wire which passes through said narrow through-hole of said closing plug so that said closing plug is slidable over the guide wire; and (C) a pushing catheter having an inner diameter smaller than the outer dimension of said closing plug when said enlarged portions are at their respective reduced size before they are enlarged to their respective original predefined larger size and shape.

9. A closing plug device as claimed in claim 8, wherein said shape memory polymer contains a radiopaque material.

10. A closing plug device which comprises:
(A) a closing plug for closing an opening in a body part of a living body, said opening in said body part including one of a patent ductus arteriosus (PDA), atrial septal defect (ASD), ventricular septal defect (VSD), aneurysm and varix, said opening having a rim defining a boundary of said opening, and said body part having an interior surface and an exterior surface adjacent said rim of said opening, the closing plug comprising:

a body portion having opposite end portions; and an enlarged portion at each opposite end portion of said body portion, said enlarged portions each having a predefined size and shape which is larger than said opening to be closed and larger than a cross sectional size of said opening to be closed; and wherein at least said enlarged portions are made of a shape memory polymer having a shape recovery temperature in the range of from 20° C. to 70° C., such that at least said enlarged portions are physically able to be reduced in size to a size to freely pass through said opening without further enlarging said opening, prior to introduction into said opening in the body part, and are able to be enlarged to their respective original predefined larger size and shape after insertion through said opening in said body part and after exposure to a temperature within said shape recovery temperature range so as to contact said interior surface and said exterior surface, respectively, of said body part adjacent said rim of said opening to close said opening and to prevent said closing plug from coming out of said closed opening;

said closing plug having a narrow through-hole therein, which extends between each of said enlarged portions and which provides effective closure of said opening of said body part, and through which a guide wire is passable between each of said enlarged portions;

(B) a catheter having an inner diameter larger than the maximum outer dimension of said closing plug when said enlarged portions are at their respective reduced size, and having said reduced size closing plug slidably received therein; and (C) a pushing wire which is slidable through the inside of the catheter for pushing said closing plug through the interior of said catheter and through the opening in said body part which is to be closed by said closing plug.

11. A closing plug device as claimed in claim 8 or 10, wherein said closing plug has a rough outer surface.

12. A closing plug device as claimed in claim 8 or 10, wherein the outer surface of said closing plug is coated with an antithrombogenic material.

* * * * *

UNITED STATES PATENT AND TRADEMARK OFFICE
CERTIFICATE OF CORRECTION

PATENT NO. : 5,192,301
DATED : March 9, 1993
INVENTOR(S) : KAMIYA et al

It is certified that error appears in the above-indentified patent and that said Letters Patent is hereby corrected as shown below:

On the Title Page,

Section [56] References Cited,

Under "U.S. Patent Documents",

Change "4,936,204" to --4,836,204--.

Signed and Sealed this

Seventh Day of June, 1994

Attest:

BRUCE LEHMAN

*Attesting Officer*     *Commissioner of Patents and Trademarks*